United States Patent [19]

Lindemann et al.

[11] 4,261,911

[45] Apr. 14, 1981

[54] PHOSPHITAINES

[75] Inventors: Martin K. O. Lindemann, Bridgewater; Raymond L. Mayhew, Summit; Anthony J. O'Lenick, Jr., Fairlawn; Robert J. Verdicchio, Succasunna, all of N.J.

[73] Assignees: Johnson & Johnson, New Brunswick; Mona Industries, Inc., Paterson, both of N.J.

[21] Appl. No.: 965,462

[22] Filed: Nov. 30, 1978

[51] Int. Cl.$^3$ ............................................. C07F 9/02
[52] U.S. Cl. ................................. 260/403; 260/945
[58] Field of Search ............................... 260/945, 403

[56] References Cited

U.S. PATENT DOCUMENTS

| 3,694,473 | 9/1972 | Eibl et al. | 260/403 |
| 3,775,446 | 11/1973 | Wegerhoff et al. | 260/403 |
| 4,181,634 | 1/1980 | Kennedy et al. | 252/545 |

FOREIGN PATENT DOCUMENTS 1388879  3/1975  United Kingdom.

Primary Examiner—Henry R. Jiles
Assistant Examiner—R. W. Ramsuer
Attorney, Agent, or Firm—Steven P. Berman

[57] ABSTRACT

Phosphitaine compounds of the formula

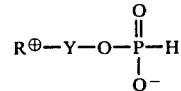

wherein R is an amidoamine reactant moiety and Y is hydroxyalkylene. The compounds are useful as surfactants.

11 Claims, No Drawings

PHOSPHITAINES

BACKGROUND OF THE INVENTION

The present invention relates to novel compositions of matter consisting of specific betaine derivatives referred to hereinafter as "phosphitaines". More particularly, this invention relates to novel amphoteric and zwitterionic betaine surfactants having at least one phosphorus-containing anion in the molecule.

Betaines and certain substituted betaines are known in the art but prior to the present invention the novel phosphitaines of this invention had not been disclosed or suggested. The phosphitaines of the present invention exhibit outstanding foaming, viscosity-building, wetting, cleansing, detergency, anti-static and emulsifying properties and are therefore useful in industrial applications calling for high performance surface active agents. The compounds are also highly stable species and are extremely well tolerated by human tissue, i.e., they exhibit exceptionally low ocular irritation and oral toxicity, and are therefore eminently suited and useful as surface active agents in personal care compositions.

THE INVENTION

The novel phosphitaine compounds of the invention may be represented by the following general formula:

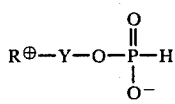

R is an amidoamine reactant moiety of the formula:

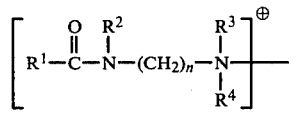

wherein $R^1$ is alkyl, alkenyl, alkoxy, or hydroxyalkyl of from 5 to 22 carbon atoms each, or aryl or alkaryl of up to 20 carbon atoms, $R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms, $R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-heterocycle, e.g., a morpholino structure, in which the Y radical is bonded to a ring atom of said N-heterocycle other than the nitrogen of the R moiety;

n is an integer from 2 to 12

The term "polyoxyalkene radical" as used above in the definition of $R^2$, $R^3$ and $R^4$ may be of the formula $(R^5-O-R^{5'})_{m'}$ wherein $R^5$ and $R^{5'}$ are alkyl of from 1 to 4 carbon atoms and $m'$ is an integer from about 2 to 10.

In addition to the foregoing definitions wherein R is amidoamine,

R may be an N-heterocyclic radical which may contain one additional hetero atom (e.g., oxygen, sulfur nitrogen) and contains 5 to 6 total ring carbon atoms; optionally said heterocyclic radical may be substituted with alkyl and/or hydroxyalkyl of up to 20 carbon atoms eadh. Typical of such N-heterocyclic radicals are imidazolyl, N-alkylmorpholino, alkylpyrimidino, alkyloxazolinyl, and the like. Such compounds may be represented by the formula:

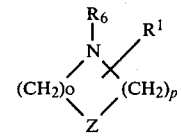

wherein

Z is N, S or O o is an integer from 0 to 3;

p is an integer from 1 to 3; provided that the sum of o+p is from 3 to 4;

$R^1$ is defined as before and is linked to a ring carbon atom; and $R^6$ is alkyl of from 2 to 6 carbon atoms which may be substituted with a hydroxyl group at the terminal or a non-terminal carbon atom.

Y may be alkylene, optionally interrupted by up to 3 oxygen atoms, of up to 12 carbon atoms, which alkylene chain may optionally be substituted with lower alkyl, alkoxy, hydroxy or hydroxyalkyl, e.g., of not more than 10 carbon atoms each.

The phosphitaine compounds of the invention can be prepared from the corresponding phosphite esters and amine reactants, as follows:

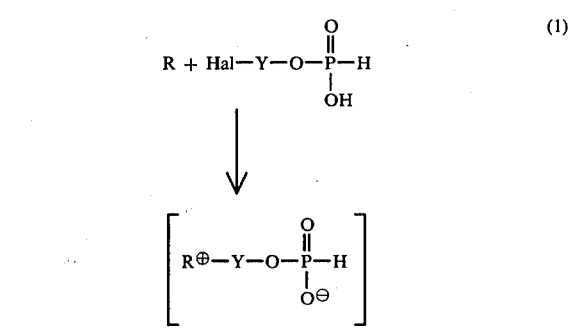

wherein
R is an amine reactant of the formulas:

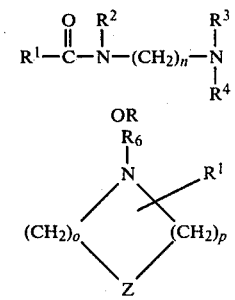

in which the radicals are defined as above.

Preparation of Intermediate "R" Reactants

The amine reactant "R" applicable to all of the above is, in general, prepared by reacting an acid with an aminoalkyl-substituted tertiary amine to result in the amidoamine function. Alternatively, an acid can be reacted with an aminoalkyl-substituted secondary amine, followed by further treatment of the reaction product with alkylene oxide. Finally, when R represents the N-heterocyclic structure, e.g., imidazolyl, this can be prepared in accordance with known techniques, e.g., as taught in U.S. Pat. No. 2,267,965.

Reaction (2) below yields the non-cyclic reactants "R" and Reaction (3) illustrates the preparation of a typical cyclic amine reactant R (Imidazolyl):

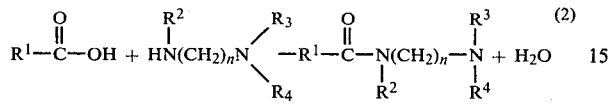  (2)

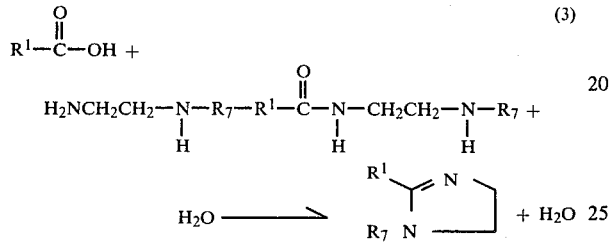  (3)

wherein, $R^1$ is defined as above and $R^7$ is alkyl of 2 to 6 carbon atoms which may be substituted with a hydroxyl group (at the terminal or a non-terminal carbon atom. This cyclic reactant can be prepared as disclosed in U.S. Pat. No. 2,267,965.

Preparation of Phosphite Ester Intermediate Reactants

The preparation of the phosphite ester intermediate reactant is conducted as illustrated below:

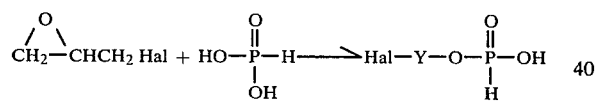

In carrying out the reaction 1 as set forth above leading to the ultimate phosphitaine compound of the invention, the amine intermediate reactant (R) is reacted with the appropriate phosphite ester intermediate reactant and these reactions are generally carried out in an aqueous system at 80°–100° C. The phosphitaine product will have a final pH at 10% of 6–8, depending on the specific nature of the product, i.e., the nature of the amine reactant employed.

These novel phosphitaines are good surfactants and quite unexpectedly exhibit good foam volume and superior foam stability in comparison to commercially available amphoteric and zwitterionic surfactants.

The compounds of this invention were tested by a "cylinder shake test" for the evaluation of foaming characteristics.

In this test solutions containing 0.1% by weight of the candidate surfactant in water of 100 ppm hardness (calcium to magnesium ratio 3:2) were used and placed in 100 ml stoppered cylinders which had been cleaned so that water drains down its walls in an unbroken film. Each cylinder filled with test solution was shaken twenty (20) times in a standard manner and net foam in ml is noted one minute and again five minutes after shaking. The tests were run in triplicate. The results were as follows:

| | Example Number | One Minute | Five Minutes |
|---|---|---|---|
| Lauric Myristic Amido Betaine | — | 67 | 60 |
| Cocamido Betaine | — | 70 | 63 |
| Coco Betaine | — | 65 | 56 |
| Lauric Myristic Amido Propyl Mono Sodium Phosphitaine | 2 | 88 | 76 |
| Cocamido Propyl Mono Sodium Phosphitaine | 1 | 79 | 70 |

The preparation of specific compounds of the invention is illustrated by the following specific examples. For simplicity, there first set forth the specific phosphite ester intermediate reactant which used in the examples, in conjunction with certain tertiary amine reactants which are specifically set forth in each example.

Phosphite Ester Intermediate Reactant

REACTANT "A"

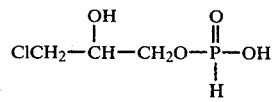

To 60.00 parts of soft water in a suitable reactor, slowly charge 21.17 parts of $NaH_2PO_3$ under good agitation. Heat to 40°–50° C. Slowly charge 18.83 parts epichlorohydrin under good agitation. Seal reactor and apply 5 PSIG nitrogen. Heat to 90°–95° C. and hold 3–4 hours. Reaction is complete when theoretical reduction in acid value has occurred. The product is an aqueous solution of a novel reactant having the above structure.

PRODUCT EXAMPLES

EXAMPLE NO. 1

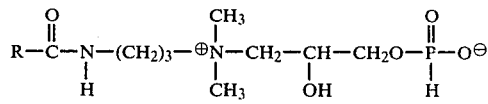

To 60.00 parts of soft water in a suitable reactor, charge 19.68 parts of Reactant "A" under good agitation. Heat to 40°–50° C. and charge 20.32 parts of 3 cocoamido propyl dimethyl amine. Under good agitation heat to 90°–95° C. and hold 4–5 hours. Reaction is complete when theoretical inorganic chloride is generated and when residual tertiary nitrogen levels become vanishingly small.

The product is an aqueous solution of the above material R=$C_7$ to $C_{17}$

EXAMPLE NO. 2

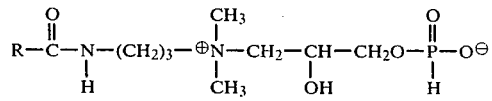

To 60.00 parts of soft water in a suitable reactor, charge 20.06 parts of Reactant "A" under good agitation. Heat to 40°–45° C. and charge 19.94 parts of a 70/30 blend of 3 lauramido propyl dimethyl amine + 3 myristamido propyl dimethyl amine under good agitation. Heat to 90°–95° C. and hold 4-5 hours. Reaction is complete when theoretical inorganic chloride is generated and when residual tertiary nitrogen levels become vanishingly small.

The product is an aqueous solution of the above material $R = 70\%\text{—}C_{11}/30\%\text{—}C_{13}$ alkyl

EXAMPLE NO. 3

$$R-\overset{O}{\underset{\|}{C}}-\underset{H}{\underset{|}{N}}-(CH_2)_3-\overset{CH_3}{\underset{\underset{CH_3}{|}}{\overset{\oplus}{N}}}-CH_2-\underset{OH}{\underset{|}{CH}}-CH_2O-\overset{O}{\underset{\underset{H}{|}}{\overset{\|}{P}}}-O^{\ominus}$$

to 60.00 parts of soft water in a suitable reactor, charge 20.82 parts of Reactant "A" under good agitation. Heat to 45°–50° C. and charge 19.18 parts of 3 lauramido propyl dimethyl amine under good agitation. Heat to 90°–95° C. and hold 4-5 hours. Reaction is complete when theoretical inorganic chloride is generated and when residual tertiary nitrogen levels become vanishingly small.

The product is an aqueous solution of the above material. $R = C_{11}$ alkyl

EXAMPLE NO. 4

$$R-\overset{O}{\underset{\|}{C}}-\underset{H}{\underset{|}{N}}-(CH_2)_3-\overset{CH_3}{\underset{\underset{CH_3}{|}}{\overset{\oplus}{N}}}-CH_2-\underset{OH}{\underset{|}{CH}}-CH_2O-\overset{O}{\underset{\underset{H}{|}}{\overset{\|}{P}}}-O^{\ominus}$$

To 60.00 parts of soft water in a suitable reactor, charge 23.10 parts of Reactant "A" under good agitation. Heat to 45°–50° C. and charge 16.9 parts of 3 caprylamido propyl dimethyl amine under good agitation. Heat to 90°–95° C. and hold 4-5 hours. Reaction is complete when theoretical inorganic chloride is generated and when residual tertiary nitrogen levels become vanishingly small.

The product is an aqueous solution of the above material $R = C_7$ alkyl

EXAMPLE NO. 5

$$R-\overset{O}{\underset{\|}{C}}-\underset{H}{\underset{|}{N}}-(CH_2)_3-\overset{CH_3}{\underset{\underset{CH_3}{|}}{\overset{\oplus}{N}}}-CH_2-\underset{OH}{\underset{|}{CH}}-CH_2O-\overset{O}{\underset{\underset{H}{|}}{\overset{\|}{P}}}-O^{\ominus}$$

To 60.00 parts of soft water in a suitable reactor, charge 24.45 parts of Reactant "A" under good agitation. Heat to 45°–50° C. and charge 15.55 parts of 3 capramido propyl dimethyl amine under good agitation. Heat to 90°–95° C. and hold 4-5 hours. Reaction is complete when theoretical inorganic chloride is generated and when residual tertiary nitrogen levels become vanishingly small.

The product is an aqueous solution of the above material $R = C_5$ alkyl

EXAMPLE NO. 6

$$R-\overset{O}{\underset{\|}{C}}-\underset{H}{\underset{|}{N}}-(CH_2)_3-\overset{CH_3}{\underset{\underset{CH_3}{|}}{\overset{\oplus}{N}}}-CH_2-\underset{OH}{\underset{|}{CH}}-CH_2O-\overset{O}{\underset{\underset{H}{|}}{\overset{\|}{P}}}-O^{\ominus}$$

To 60.00 parts of soft water in a suitable reactor, charge 18.13 parts of Reactant "A" under good agitation. Heat to 45°–50° C. and charge 21.87 parts of 3 oleamido propyl dimethyl amine under good agitation. Heat to 90°–95° C. and hold 4-5 hours. Reaction is complete when theoretical inorganic chloride is generated and when residual tertiary nitrogen levels become vanishingly small.

The product is an aqueous solution of the above material $R = C_{17}$ alkyl

EXAMPLE NO. 7

$$R-\overset{O}{\underset{\|}{C}}-\underset{H}{\underset{|}{N}}-(CH_2)_3-\overset{CH_2CH_3}{\underset{\underset{CH_2CH_3}{|}}{\overset{\oplus}{N}}}-CH_2-\underset{OH}{\underset{|}{CH}}-CH_2O-\overset{O}{\underset{\underset{H}{|}}{\overset{\|}{P}}}-O^{\ominus}$$

To 60.00 parts of soft water in a suitable reactor, charge 21.02 parts of Reactant "A" under good agitation. Heat to 45°–50° C. and charge 18.98 parts of 3 cocamido propyl di ethyl amine under good agitation. Heat to 90°–95° C. and hold 4-5 hours. Reaction is complete when theoretical inorganic chloride is generated and when residual tertiary nitrogen levels become vanishingly small.

The product is an aqueous solution of the above material $R = C_7$–$C_{17}$ alkyl

EXAMPLE NO. 8

(imidazoline structure with $\overset{\oplus}{N}-CH_2-CH(OH)-CH_2O-P(=O)(O^{\ominus})-H$ and $CH_2CH_2OH$ substituent)

To 60.00 parts of soft water in a suitable reactor, charge 20.66 parts of Reactant "A" under good agitation. Heat to 45°–50° C. and charge 19.34 parts of 1 hydroxyethyl 2 alkyl 2 imidazoline (alkyl being $C_7$ to $C_{17}$) under good agitation. Heat to 90°–95° C. and hold 4-5 hours. Reaction is complete when theoretical inorganic chloride is generated and when residual tertiary nitrogen levels become vanishingly small.

The product is an aqueous solution of the above material. $R = C_7$–$C_{17}$ alkyl

What is claimed is:

1. Phosphitaine compound of the formula $$\overset{\oplus}{R}-Y-O-\overset{O}{\underset{\underset{O^-}{|}}{\overset{\|}{P}}}-H$$

wherein

R is an amidoamine reactant moiety of the formula:

$$\left[R^1-\overset{O}{\overset{\|}{C}}-\underset{R^2}{\underset{|}{N}}-(CH_2)_n-\underset{R^4}{\underset{|}{\overset{R^3}{\underset{|}{N}}}}\text{—}\right]^{\oplus}$$

wherein $R^1$ is alkyl, alkenyl, alkoxy, or hydroxyalkyl of from 5 to 22 carbon atoms each, R² is hydrogen or alkyl, hydroxyalkyl or alkenyl of up to 6 carbon atoms each, R³ and R⁴, which may be the same or different, are selected from alkyl, hydroxyalkyl, carboxyalkyl of up to 6 carbon atoms in each alkyl moiety, n is an integer from 2 to 12;

Y is hydroxy alkylene of up to 12 carbon atoms.

2. Phosphitaine compound as claimed in claim 1 wherein

R is an amidoamine reactant moiety of the formula

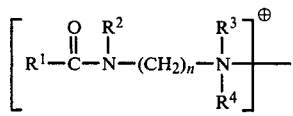

wherein

R¹, R², and n are as previously defined and R³ and R⁴ are methyl.

3. Phosphitaine compound as claimed in claim 1 wherein

R¹ is alkyl

R² is hydrogen or alkyl

R³ and R⁴ are selected from alkyl and hydroxyalkyl.

4. Phosphitaine compound as claimed in claim 1 wherein R¹ is hydroxyalkyl.

5. Phosphitaine compound as claimed in claim 1 wherein Y is hydroxypropylene.

6. Phosphitaine compound as claimed in claim 1 of the formula

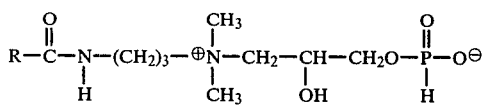

wherein

R is alkyl from 7 to 17 carbon atoms.

7. Phosphitaine compound as claimed in claim 1 of the formula

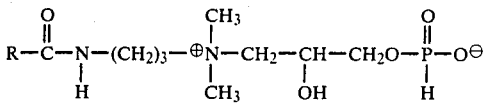

wherein

R is alkyl from 11 to 13 carbon atoms.

8. Phosphitaine compound as claimed in claim 1 of the formula

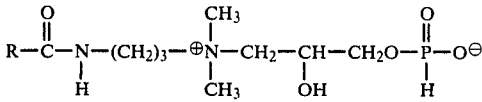

wherein

R is alkyl of 11 carbon atoms.

9. Phosphitaine compound as claimed in claim 1 of the formula

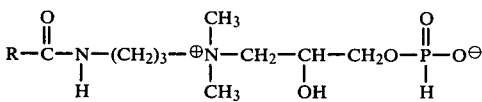

wherein

R is alkyl of 7 carbon atoms.

10. Phosphitaine compound as claimed in claim 1 of the formula

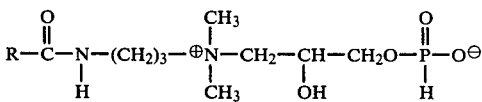

wherein

R is alkyl of 5 carbon atoms.

11. Phosphitaine compound as claimed in claim 1 of the formula

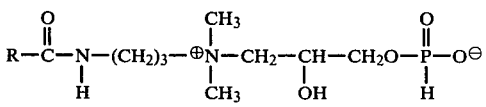

wherein

R is alkyl of 17 carbon atoms.

* * * * *